United States Patent [19]

Pings

[11] Patent Number: 5,482,703
[45] Date of Patent: Jan. 9, 1996

[54] HAIR CONDITIONING COMPOSITIONS

[75] Inventor: Keith D. Pings, Cincinnati, Ohio

[73] Assignee: The Proctor & Gamble Company, Cincinnati, Ohio

[21] Appl. No.: 134,130

[22] Filed: Oct. 12, 1993

Related U.S. Application Data

[63] Continuation of Ser. No. 560,260, Jul. 25, 1990, abandoned, which is a continuation of Ser. No. 433,408, Nov. 3, 1989, abandoned, which is a continuation of Ser. No. 589,975, Mar. 15, 1984, abandoned.

[51] Int. Cl.$^6$ .................................................. A61K 7/075
[52] U.S. Cl. ........................................................ 454/70.12
[58] Field of Search ............................................ 424/70.12

[56] References Cited

U.S. PATENT DOCUMENTS

| | | | |
|---|---|---|---|
| 4,073,880 | 2/1978 | Pader et al. | 424/66 |
| 4,213,960 | 7/1980 | Grollier et al. | 424/47 |
| 4,311,695 | 1/1982 | Starch | 424/184 |
| 4,342,742 | 8/1982 | Sebag et al. | 424/359 |
| 4,344,763 | 8/1982 | Tolgyesi et al. | 8/127.51 |
| 4,374,825 | 2/1983 | Bolich, Jr. et al. | 424/70 |
| 4,387,090 | 6/1983 | Bolich, Jr. | 424/70 |
| 4,421,769 | 12/1983 | Dixon et al. | 424/358 |
| 4,423,041 | 12/1983 | Clum et al. | 424/184 |
| 4,493,824 | 1/1985 | Abe | 424/70 |

FOREIGN PATENT DOCUMENTS

| | | | |
|---|---|---|---|
| 727588 | 2/1966 | Canada | 424/70 |
| 2808830 | 9/1978 | Germany | 424/70 |
| 3206448 | 10/1982 | Germany | 424/70 |
| 0197609 | 9/1976 | Japan | 424/70 |
| 56092808A | 7/1981 | Japan . | |
| 0169614 | 12/1981 | Japan | 424/70 |
| 0200308 | 12/1982 | Japan | 424/70 |
| 832813A | 2/1983 | Japan . | |
| 535579 | 5/1973 | Switzerland | 424/70 |
| 2066659 | 7/1981 | United Kingdom | 424/70 |
| 1598567 | 9/1981 | United Kingdom | 424/70 |

*Primary Examiner*—C. Warren Ivy
*Assistant Examiner*—Evelyn Huang
*Attorney, Agent, or Firm*—Leonard W. Lewis; William J. Winter

[57] ABSTRACT

Compositions, for conditioning human hair, comprising from about 0.1% to about 10% of a silicone conditioning agent, from about 0.01% to about 10% of a dimethicone copolyol, from about 0.1% to about 10% of a lipid vehicle material, from about 0.05% to about 5% of a cationic surfactant vehicle material, and the balance of water. Preferably the lipid vehicle materials are fatty alcohols or fatty esters. Also preferably, the silicone conditioning agent is an unsubstituted, amine substituted, or alkoxy substituted polydimethyl siloxane.

16 Claims, No Drawings

HAIR CONDITIONING COMPOSITIONS

This is a continuation of application Ser. No. 433,408 filed on Nov. 3, 198, now abandoned.

BACKGROUND OF THE INVENTION

The present invention relates to compositions for application to and care of human hair. More particularly, it relates to improved compositions for conditioning hair.

Products which improve the appearance, feel, and manageability of hair have gained increasing acceptance and popularity with consumers. The utility of such compositions is particularly important with the use of such hair treatments as permanent waving, dyeing, teasing, and bleaching. The physical condition of hair can also be affected by atmospheric conditions, such as sunlight, which may cause photo-catalyzed oxidation. These factors may result in hair with poor texture, which is difficult to manage and comb, whether wet or dry.

Accordingly, compositions which "condition" hair generally improve the manageability, appearance and feel of hair, as by reducing dry static and increasing the ease of combing both wet and dry hair. Such conditioning products are well known. Some are "rinse-type" products which are applied and rinsed off the hair, while others are "deep conditioners" which are allowed to remain on the hair for extended periods of time. Many conditioning products contain long chain quaternary ammonium compounds combined with fatty materials, such as fatty alcohols. Such compositions are disclosed, for example, in U.S. Pat. No. 3,155,591, Hilfer, issued Nov. 3, 1964 and U.S. Pat. No. 4,269,824, Villamarin, et al., issued May 26, 1981. While such products have particularly good cosmetic in-use and rheologic characteristics, they may leave the hair greasy or oily, and subject to resoiling with dirt and sebum. These undesirable characteristics are, unfortunately, related to the conditioning benefit, since such products (as they are known in the art) inherently lead to deposition of both vehicle and conditioning active materials on the hair.

A variety of compositions have been developed which attempt to provide good conditioning benefits while maintaining acceptable cosmetic in-use and rheologic characteristics. In particular, volatile silicone oils are well known for use in conditioning products. For example, British Patent Specification 1,598,567, Lewis, et al., published Sep. 23, 1981, discloses hair conditioners containing volatile silicones and certain surfactants. (An essential feature of these compositions is their freedom from fatty materials and quaternary ammonium compounds.) British Patent Specification 999,222, published Jul. 21, 1965, discloses organosilicone polymers in water-alcohol mixtures for use as hair conditioners. U.S. Pat. No. 4,374,825, Bolich, et al., issued Feb. 22, 1983, discloses conditioners containing hydrocarbon or silicone conditioning agents, certain nonionic water-soluble thickening agents, and a cationic conditioning agent. U.S. Pat. No. 4,387,090, Bolich, issued Jun. 7, 1983, discloses conditioning compositions containing volatile hydrocarbon or silicone conditioning agents and certain polymeric thickening agents. U,K, Patent Application 2,068,659, Abe, published Jul. 15, 1981, discloses conditioning hair rinse compositions comprising quaternary ammonium salts, silicone materials, and propylene glycol.

It has now been discovered that hair conditioning formulations containing a dimethicone copolyol and a silicone conditioning agent, in a gel vehicle consisting of a lipid material and a cationic surfactant, have improved hair care benefits while maintaining excellent in-use characteristics. In particular, such compositions exhibit lower resoiling of hair after use than similar compositions that do not contain the dimethicone copolyol. Thus, such products provide excellent conditioning benefits with low resoiling, while maintaining preferred theology,

SUMMARY OF THE INVENTION

The present invention provides hair conditioning compositions comprising:

(a) from about 0.1% to about 10% of a silicone conditioning agent;

(b) from about 0.01% to about 10% of a dimethicone copolyol;

(c) from about 0.1% to about 10% of a lipid vehicle material;

(d) from about 0.05% to about 5% of a cationic surfactant vehicle material; and (e) the balance of water.

Preferably, the lipid vehicle materials are fatty alcohols or fatty esters.

These products are preferably used as rinse-type conditioners. Thus, the present invention also provides methods of conditioning hair by applying the compositions to freshly shampooed hair and rinsing the composition from the hair.

DESCRIPTION OF THE INVENTION

The conditioning compositions of this invention contain five essential ingredients: a silicone hair conditioning agent; a dimethicone copolyol; a lipid vehicle material; a cationic surfactant vehicle material; and water. These compositions encompass any such composition intended for human use in order to condition hair. Depending upon the specific conditioning benefits and product theology desired, specific essential components may be selected, and other optional ingredients may be incorporated, in forming the final conditioning product. The balance of the product is made up of water, preferably distilled water.

Specifically, the hair conditioners of the present invention comprise:

(a) from about 0.1% to about 10% of a silicone conditioning agent;

(b) from about 0.01% to about 10% of a dimethicone copolyol;

(c) from about 0.1% to about 10% of a lipid vehicle material;

(d) from about 0.05% to about 5% of a cationic surfactant vehicle material; and (e) the balance of water.

(All percentages herein are by weight of total composition.) Preferably, the lipid vehicle material is incorporated at levels of from about 1% to about 3% and the cationic surfactant vehicle material is incorporated at levels of from about 0.2% to about 3%. The silicone conditioning agent is preferably incorporated at levels of from about 0.25% to about 1.5%, and the dimethicone copolyol is preferably incorporated at levels of from about 0.1% to about 2.0%.

Silicone Conditioning Agent

The compositions of the present invention include one or more silicone-containing materials which impart conditioning benefits to human hair when applied in the present compositions. (As used herein, the term "silicone conditioning agent" refers to such silicone conditioning materials, singly or in combination.) Non-volatile silicones are preferred.

Preferred silicone conditioning agents include the polydimethylsiloxanes, more preferably, the linear polydimethylsiloxanes of the general formula:

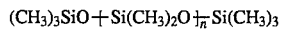

$$(CH_3)_3SiO + Si(CH_3)_2O \}_{\overline{n}} Si(CH_3)_3$$

wherein n is from 1 to 15,000, preferably from 20 to 7000. Preferred polydimethylsiloxanes are unsubstituted or are vinyl, phenyl, carboxy, alkoxy, mercapto, alkyl, or amino substituted. Particularly preferred silicone conditioning agents include the unsubstituted and the amino or alkoxy substituted linear polydimethylsiloxanes, and mixtures thereof.

Examples of silicone oils useful in the present invention include Dow Corning 200 Fluid and Dow Corning Q2-8075 Aminofunctional Fluid (manufactured by the Dow Corning Corporation); Silicone Copolymer F-755 (manufactured by SWS Silicones Corp. ), and SE 76 Silicone Gum (manufactured by General Electric). Polydimethylsiloxane conditioning agents are also disclosed in the following documents, all incorporated by reference herein: U.S. Pat. No. 4,387,097, Bolich, Jr., issued Jun. 7, 1983; U.S. patent application Ser. No. 573,780, Cobb, filed Jan. 25, 1984; British Specification 2,066,659, Abe, published Jul. 15, 1981; Wendel, et al, "Organofunctional Silicones for Personal Care Applications", 98 *Cosmetics & Toiletries* 103–106 (1983); and Todd, et al., "Volatile Silicone Fluids for Cosmetics", 91 *Cosmetics & Toiletries* 27–32 (1976).

Dimethicone Copolyol

The compositions of the present invention also contain a silicone-containing material (specifically, one or more polyalkylene oxide modified dimethylpolysiloxanes, herein referred to as a "dimethicone copolyol") which acts as a antiresoiling agent. These dimethicone copolyols reduce deposition of the vehicle materials (lipid vehicle materials and/or cationic surfactant vehicle materials) on the hair. The dimethicone copolyols include the polyalkylene oxide modified dimethylpolysiloxanes of the following formulae:

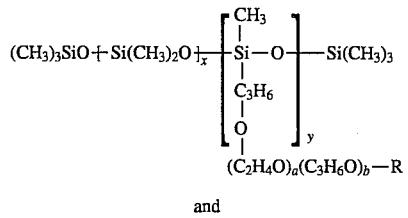

and $$R'-Si \{ + OSi(CH_3)_2 ]_{\overline{x}} (OC_2H_4)_a - (OC_3H_6)_b - OR" ]_3$$

wherein R is hydrogen, an alkyl group having from 1 to about 12 carbon atoms, an alkoxy group having from 1 to about 6 carbon atoms or a hydroxyl group; R' and R" are alkyl groups having from 1 to about 12 carbon atoms; x is an integer of from 1 to 100, preferably from 20 to 30; y is an integer of 1 to 20, preferably from 2 to 10; and a and b are integers of from 0 to 50, preferably from 20 to 30.

Dimethicone copolyols among those useful herein are disclosed in the following patent documents, all incorporated by reference herein: U.S. Pat. No. 4,122,029, Gee, et al., issued Oct. No. 24, 1978; U.S. Pat. No. 4,265,878, Keil, et al., issued May 5, 1981; and U.S. Pat. No. 4,421,769, Dixon, et al., issued Dec. 20, 1983. Such dimethicone copolyol materials are also disclosed, in hair compositions, in British Patent Application 2,066,659, Abe, published Jul. 15, 1981 (incorporated by reference herein) and Canadian Patent 727,588, Kuehns, issued Feb. 8, 1966 (incorporated by reference herein). Commercially available dimethicone copolyols, useful herein, include Silwet Surface Active Copolymers (manufactured by the Union Carbide Corporation); Dow Corning Silicone Surfactants (manufactured by the Dow Corning Corporation); Silicone Copolymer F-754 (manufactured by SWS Silicones Corp.); and Rhodorsil 70646 Fluid (manufactured by Rhone Poulenc, Inc.). Dow Corning 190 Silicone Surfactant is a preferred dimethicone copolyol.

Vehicle Materials

The present invention includes a gel-type vehicle for the silicone conditioning agents. The vehicle comprises two essential components: a lipid vehicle material and a cationic surfactant vehicle material. Such gel-type vehicles are generally described in the following documents, all incorporated by reference herein: Barry, "The Self Bodying Action of the Mixed Emulsifier Sodium Dodecyl Sulfate/Cetyl Alcohol", 28 *J. of Colloid and Interface Science* 82–91 (1968); Barry, et al., "The Self-Bodying Action of Alkyltrimethylammonium Bromides/Cetostearyl Alcohol Mixed Emulsifiers; Influence of Quaternary Chain Length", 35 *J. of Colloid and Interface Science* 689–708 (1971); and Barry, et al., "Rheology of Systems Containing Cetomacrogol 1000-Cetostearyl Alcohol, I. Self Bodying Action", 38 *J. of Colloid and Interface Science* 616–625 (1972).

Lipid Vehicle Material:

The vehicles of the present invention incorporate one or more lipid materials, (herein referred to as comprising a "lipid vehicle material", singly or in combination) which are essentially water-insoluble, and contain hydrophobic and hydrophilic moeities. Lipid vehicle materials include naturally or synthetically-derived acids, acid derivatives, alcohols, esters, ethers, ketones, and amides with carbon chains of from 12 to 22, preferably from 16 to 18, carbon atoms in length. Fatty alcohols and fatty esters are preferred; fatty alcohols are particularly preferred.

Lipid vehicle materials among those useful herein are disclosed in *Bailey's Industrial Oil and Fat Products*, (3d edition, D. Swern, ed. 1979) (incorporated by reference herein ). Fatty alcohols included among those useful herein are disclosed in the following documents, all incorporated by reference herein: U.S. Pat. No. 3,155,591, Hilfer, issued Nov. 3, 1964; U.S. Pat. No. 4,165,369, Watanabe, et al., issued Aug. 21, 1979; U.S. Pat. No. 4,269,824, Villamarin, et al., issued May 26, 1981; British Specification 1,532,585, published Nov. 15, 1978; and Fukushima, et al., "The Effect of Cetostearyl Alcohol in Cosmetic Emulsions", 98 *Cosmetics & Toiletries* 89–102 (1983). Fatty esters included among those useful herein are disclosed in U.S. Pat. No. 3,341,465, Kaufman, et al., issued Sep. 12, 1967 (incorporated by reference herein.)

Preferred esters for use herein include cetyl palmitate and glycerolmonostearate. Cetyl alcohol and stearyl alcohol are preferred alcohols. A particularly preferred lipid vehicle material is comprised of a mixture of cetyl alcohol and stearyl alcohol containing from about 55% to about 65% (by weight of mixture) of cetyl alcohol.

Cationic Surfactant Vehicle Material:

The gel-type vehicle of the present invention includes one or more cationic surfactants, herein referred to as comprising (either singly or in combination) a "cationic surfactant material". Such surfactants contain amino or quaternary ammonium hydrophilic moeities which are positively charged when dissolved in the aqueous composition of the present invention. Cationic surfactant vehicle materials among those useful herein are disclosed in the following documents, all incorporated by reference herein: M.C. Publishing Co., *McCutcheon's, Detergents & Emulsifiers*, (North American edition 1979); Schwartz, et al., Surface Active Agents, Their Chemistry and Technology, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983.

Among the quaternary ammonium-containing cationic surfactant materials useful herein are those of the general formula:

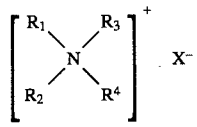

wherein $R_1$ is hydrogen, an aliphatic group of from 1 to 22 carbon atoms, or an aromatic, aryl or alkylaryl group having from 12 to 22 carbon atoms; $R_2$ is an aliphatic group having from 1 to 22 carbon atoms; $R_3$ and $R_4$ are each alkyl groups having from 1 to 3 carbon atoms, and X is an anion selected from halogen, acetate, phosphate, nitrate and alkylsulfate radicals. The aliphatic groups may contain, in addition to carbon and hydrogen atoms, ether linkages, and other groups such as amido groups.

Other quaternary ammonium salts useful herein are of the formula:

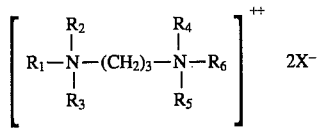

wherein $R_1$ is an aliphatic group having from 16 to 22 carbon atoms, $R_2$, $R_3$, $R_4$, $R_5$ and $R_6$ are selected from hydrogen and alkyl having from 1 to 4 carbon atoms, and X is an ion selected from halogen, acetate, phosphate, nitrate and alkyl sulfate radicals. Such quaternary ammonium salts include tallow propane diammonium dichloride.

Preferred quaternary ammonium salts include dialkyldimethylammonium chlorides, wherein the alkyl groups have from 12 to 22 carbon atoms and are derived from long-chain fatty acids, such as hydrogenated tallow fatty acid. (Tallow fatty acids give rise to quaternary compounds wherein $R_1$ and $R_2$ have predominately from 16 to 18 carbon atoms. ) Examples of quaternary ammonium salts useful in the present invention include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium, acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di(hydrogenated tallow) dimethyl ammonium chloride is a particularly preferred quaternary ammonium salt.

Salts of primary, secondary and tertiary fatty amines are also preferred cationic surfactant vehicle materials. The alkyl groups of such amines preferably have from 12 to 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate and N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981 (incorporated by reference herein.)

Non-Essential Components

The compositions of this invention preferably contain optional components which may modify the physical and performance characteristics of the conditioning product. Such components include additional surfactants, salts, buffers, thickeners, solvents, opacifiers, pearlescent aids, preservatives, fragrance, colorants, dyes, pigments, chelators, sunscreens, vitamins, and medicinal agents. Optional components that are among those useful herein are disclosed in U.S. Pat. No. 4,387,090, Bolich, Jr., issued Jun. 7, 1983, incorporated by reference herein.

The compositions of the present invention may contain optional surfactant materials, at levels such that the total level of surfactant present in the composition (including the essential cationic surfactant vehicle material, described above) is from about 0.05% to about 5%. These optional surfactant materials may be anionic, nonionic or amphoteric, such as ceteareth-20, steareth-20, sorbitan monoesters, sodium tallow alkylsulfate and tallow betaine. Optional surfactant materials are described in the following documents, all incorporated by reference herein: M. C. Publishing Co., *McCutcheon's Detergents & Emulsifiers*, (North American edition, 1979); Schwartz, et al.,*Surface Active Agents, Their Chemistry and Technology* (1949); and U.S. Pat. No. 3,929,678, Laughlin, et al., issued Dec. 30, 1975.

Preferred optional surfactant materials, useful herein, are nonionic. Such surfactants are most commonly produced by the condensation of an alkylene oxide (hydrophilic in nature) with an organic hydrophobic compound, which is usually aliphatic or alkyl aromatic in nature. The length of the hydrophilic or polyalkylene moiety which is condensed with any particular hydrophobic compound can be readily adjusted to yield a water-soluble compound having the desired degree of balance between hydrophilic and hydrophobic elements. Such nonionic surfactants include polyethylene oxide condensates of alkyl phenols, condensation products of aliphatic alcohols with ethylene oxide, condensation products of ethylene oxide with a hydrophobic base formed by condensation of propylene oxide with propylene glycol, and condensation products of ethylene oxide with the product resulting from the reaction of propylene oxide and ethylene diamine. Another variety of nonionic surfactant is the non-polar nonionic, typified by the amine oxide surfactants. Preferred nonionic surfactants include ceteareth-20, steareth-20 and ceteth-2.

Salts and buffers may also be added in order to modify the product rheology. For example, salts such as potassium chloride and sodium chloride, may be added at levels of from about 0.001% to about 1%. Buffers, such as citrate or phosphate buffers, may also be used. Preferably the pH of the present compositions modified to a pH of from about 3 to about 10, preferably from about 3 to about 7.

Optional components may be incorporated which provide additional conditioning benefits. For example, proteins may be added at levels of from about 0.1% to about 10%. Cationic proteins may also serve as surfactant vehicle materials in the present invention.

Thickening agents are also preferred optional components useful in the present invention. Such thickeners include nonionic thickening agents, incorporated at levels from about 0.1% to about 8%. Such agents are polymers which exhibit viscosities exceeding about 200 poises at low shear (about 10×2 sec $^{-1}$). Included among such polymers are polyoxyethylene, guargum, methylcellulose, methyl hydroxy propyl cellulose, polypropyl cellulose, polypropyl hydroxy ethyl cellulose, hydroxy ethyl cellulose, starches and starch derivatives, and mixtures thereof. Nonionic thickening agents are disclosed in U.S. patent application Ser. No. 432,199, Bolich, et al., filed Oct. 1, 1982, incorporated by reference herein.

Methods of Manufacture

The conditioning compositions of the instant invention can be prepared by methods well known in the art. Specific procedures for forming compositions may vary, however, depending upon such factors as the particular components used and the product theology that is desired.

In general, compositions may be made by simple admixture of components into heated water, cooling, and milling. While the aqueous bulk mixture is generally maintained, during the initial admixture of components, at a temperature above the melting point of the highest, melting component, the temperature may have to be reduced before adding volatile or other temperature-sensitive components. Certain components may be premixed and then added to the aqueous batch mixture. For example, formulation of conditioning compositions containing high molecular weight silicone conditioning agents may be facilitated by premixing the silicone conditioning agent with a volatile silicone oil.

Methods of Use

The hair conditioning compositions of the present invention are preferably used as a rinse on freshly shampooed hair. Preferably all shampoo is rinsed from the hair prior to application of the conditioning product. Thus, the present invention provides methods of conditioning hair, comprising the steps of:

(a) applying from about 1 gram to about 60 grams of a composition of the present invention to freshly shampooed hair; and (b) rinsing the composition from the hair.

Preferably, from about 5 grams to about 30 grams of the composition are applied. The product is preferably allowed to remain on the hair for a time up to about 5 minutes.

The following non-limiting examples illustrate the compositions, processes, and uses of the present invention.

EXAMPLE I

A hair conditioner, according to the present invention, was made comprising:

| Component | Weight % |
| --- | --- |
| Dow Corning Q2-8075[1] | 0.50 |
| Dow Corning 190 Silicone Surfactant[2] | 0.50 |
| cetyl alcohol | 1.13 |
| stearyl alcohol | 0.75 |
| Adogen 442 - 100P[3] | 1.05 |
| Ceteareth-20[4] | 0.35 |
| glycerol monostearate | 0.25 |
| Lexamine S-13[5] | 0.50 |
| fragrance | 0.25 |
| citric acid | 0.13 |
| preservative | 0.03 |
| distilled water | 94.56 |

[1] trimethylsilylamodimethicone, sold by Dow Corning Corporation
[2] dimethicone copolyol, sold by Dow Corning Corporation
[3] di(hydrogenated tallow) dimethyl ammonium chloride, sold by Sherex Chemical Company, Inc.
[4] ethoxylated cetostearyl alcohol
[5] stearamido propyl dimethyl amine, sold by Inolex Corporation All materials, except the preservative and fragrance, were added to the distilled water, maintained at a temperature of from 65° C. to 74° C. This mixture was then stirred for 15 minutes. After the solution was cooled to approximately 49° C., the fragrance and preservative were added. The mixture was then cooled to approximately 38° C. and milled under high shear for approximately 2 minutes using a conventional milling apparatus.

Approximately 20 g. of the hair conditioning product thus formed is applied to freshly shampooed and rinsed hair. The composition is then spread over the hair and allowed to stand for approximately 1 minute. Thereafter, the product is rinsed from the hair, leaving the hair with conditioning benefits.

EXAMPLE II

A hair conditioner, according to the present invention, was made comprising:

| Component | Weight % |
| --- | --- |
| stearoxy dimethicone | 1.00 |
| dimethicone oil (12,500 cs) | 1.00 |
| Silwet L-7002[1] | 1.00 |
| cetearyl alcohol | 3.00 |
| stearyl dimethyl benzyl ammonium chloride | 2.00 |
| hydroxy ethyl cellulose | 0.50 |
| Peptein 2000[2] | 0.50 |
| Panthenol[3] | 0.50 |
| fragrance | 0.50 |
| titanium dioxide | 0.10 |
| phosphoric acid | 0.05 |
| preservative | 0.05 |
| colorant | 0.05 |
| distilled water | 89.75 |

[1] dimethicone copolyol, sold by Union Carbide Corporation
[2] hydrolyzed animal protein, sold by Geo. A. Hormel & Co.

-continued

| Component | Weight % |
|---|---|
| [3]pantothenyl alcohol, provitamin of the B-complex vitamin pantothenic acid, sold by Hoffman-LaRoche, Inc. | |

A conditioning product was made, as comprised above, in a manner similar to that described in Example I. This product, when applied to hair, is useful as a conditioner.

EXAMPLE III

A hair conditioner, according to the present invention, is made comprising:

| Component | Weight % |
|---|---|
| $D_5$ cyclomethicone | 8.00 |
| dimethicone oil | 1.00 |
| Silwet L-720* | 2.00 |
| cetyl palmitate | 1.00 |
| glycerol monostearate | 3.00 |
| dicetyldimonium chloride | 2.00 |
| perfume | 0.50 |
| colorant | 0.11 |
| preservative | 0.03 |
| distilled water | 82.36 |

*dimethicone copolyol, sold by Union Carbide Corporation

A conditioning product, as comprised above, is made in a manner similar to that described in Example I. This product, when applied to human hair, is useful as a hair conditioner.

EXAMPLE IV

A hair conditioner, according to the present invention, was made comprising:

| Component | Weight % |
|---|---|
| dimethicone oil (12,500 cs) | 1.00 |
| Rhodorsil 70646 Fluid* | 1.00 |
| cetyl alcohol | 1.50 |
| stearyl alcohol | 1.50 |
| Lexamine S-13 | 1.00 |
| ceteth-20 | 0.20 |
| fragrance | 0.50 |
| citric acid | 0.20 |
| preservative | 0.03 |
| distilled water | 93.07 |

*dimethicone copolyol, sold by Rhone-Poulenc, Inc.

A hair conditioning product was made, as comprised above, in a manner similar to that described in Example I. This product, when applied to human hair, is useful as a conditioner.

In the above example, stearylamine, diethylaminopropyl stearamide, dimethyl stearamine, tridcylamine, ethyl stearamine, N-tallowpropane diamine, myristylamine, ethoxylated stearylamine, dihydroxyethyl stearylamine and arachidylbehenylamine are substituted, respectively, for the Lexamine S-13 stearamidopropyl dimethylamine, with substantially similar results.

EXAMPLE V

A hair conditioner, according to the present invention, was made comprising:

| Component | Weight % |
|---|---|
| $D_5$ cyclomethicone | 2.00 |
| SE-76 Silicone Gum[1] | 0.15 |
| Silicone Copolymer F-755[2] | 0.50 |
| Dow Corning 190 Silicone Surfactant | 0.50 |
| cetyl alcohol | 1.25 |
| stearyl alcohol | 1.25 |
| Adogen 442 | 0.75 |
| Lexamine S-13 | 0.75 |
| hydroxyethyl cellulose | 0.50 |
| fragrance | 0.25 |
| citric acid | 0.13 |
| preservative | 0.03 |
| distilled water | 91.94 |

[1]dimethicone gum, sold by General Electric
[2]stearoxy dimethicone, sold by SWS Silicones Corporation A hair conditioning product was made in a manner similar to that described in Example I, except for processing of the cyclomethicone/dimethicone gum materials. These silicone agents were premixed under heat and agitation to form a gum solution. The gum solution was added to the conditioning product batch mix after the batch solution was cooled to approximately 48° C. The final product, when applied to human hair, is useful as a conditioning agent.

In the above example ditallow dimethyl ammonium chloride, stearyl trimethyl ammonium chloride, cetyl trimethyl ammonium chloride, distearyl dimethyl ammonium chloride, dicetyl dimethyl ammonium chloride and ditallow dipropyl ammonium phosphate are substituted w respectively, for the Adogen 442 di(hydrogenated tallow) dimethyl ammonium chloride, with substantially similar results.

EXPERIMENT I

Four formulations were prepared which had the same composition as the products described in Example I, but with the following variation in levels of silicone materials present.

| | Weight % | |
|---|---|---|
| Composition | silicone conditioning active | dimethicone copolyol |
| A | 0 | 0 |
| B | 0 | 0.5 |
| C | 0.5 | 0 |
| D | 0.5 | 0.5 |

(To the extent that these compositions contained levels of silicone conditioning active or dimethicone copolyol lower than in Composition D, the amount of water was increased.) Each of these compositions was applied to hair switches in order to determine the levels of vehicle materials and silicone-containing materials that remained on the hair after rinsing.

Specifically, 20 switches of hair, weighing 4 grams and approximately 203 mm long, were prepared by stripping in a 90:10 mixture of methylene chloride and methanol, for one hour. The switches were then washed with a conventional shampoo for 30 seconds, rinsed for 30 seconds, shampooed again for 30 seconds, and finally rinsed for 60 seconds.

The shampoo/rinse/shampoo/rinse sequence was then repeated. One of Compositions A, B, C or D was then applied to each switch of hair. (A total of 5 switches were used to evaluate each composition.) The respective test composition was dispersed thoroughly throughout each switch, and then the switches were rinsed for 30 seconds. (Gloves were worn throughout the treatment procedure, and changed between each product treatment.) The switches were then air dried.

Samples were cut from each dried switch, placed in tared vials, and weighed. Ten milliliters of a suitable solvent, such as a 90:10 methylene chloride/methanol solvent mix, were added to each vial, and the vials agitated for approximately 18 hours. The extracted solution was then filtered and placed in tared vial. The level of cationic surfactant was then determined using High Performance Liquid Chromatography. The amount of silicone-containing material was determined using Atomic Adsorption Spectroscopy.

The following table presents the levels (in micrograms per milligram of hair) of cationic surfactant and silicone-containing material present in the switches treated with each Composition.

TABLE I

| Composition | cationic surfactant | silicone-containing material |
|---|---|---|
| A | 0.307 | — |
| B | 0.196 | 0* |
| C | 0.286 | 0.19 |
| D | 0.176 | 0.18 |

*less than the 0.02 μg/mg minimum detection level

The levels of cationic surfactant vehicle material deposited from Compositions B and D (containing a dimethicone copolyol) were significantly different than the levels deposited from Compositions A and C (without the silicone copolymer), at a 95% confidence level (LSD=0.070). This data thus demonstrates that the dimethicone copoylols of the present invention significantly reduce the levels of cationic surfactant vehicle material deposited on hair during use. This data also shows that the dimethicone copolyol material is not, itself, deposited in significant amounts. Therefore, this data demonstrates that the dimethicone copolyol reduces undesirable deposition of vehicle materials on treated hair without significantly reducing the deposition of the silicone conditioning agent.

EXPERIMENT II

Four formulations (A, B, C and D) were made, each composed identically to those tested in Experiment I. The compositions were applied to hair switches. After the switches were soiled with synthetic sebum, the switches were then graded by expert judges in order to determine the cleanliness/dirtiness of the switches.

In particular, 48 switches of hair were prepared by rinsing each for 15 seconds at approximately 38° C., washing for 30 seconds using a conventional shampoo, rinsing for 30 seconds, and then soaking for one hour using a 90:10 methylene chloride/methanol mixture.

Each switch was again rinsed for 15 seconds, washed for 30 seconds with a conventional shampoo, rinsed for 30 seconds, washed again for 30 seconds, and finally rinsed for 60 seconds. Thereafter, one of each of Composition A, B, C or D was applied to each switch, using 1 milliliter of product per gram of hair. Composition A (vehicle only) was applied to 18 switches, Composition D (of the present invention) was applied to 12 switches, and Compositions B and C were applied to 6 switches, each. The rinse formulations were then dispersed throughout their respective hair switches, and allowed to remain for 60 seconds. The switches were combed and rinsed for 60 seconds.

The switches were allowed to dry overnight and then weighed. A solution of synthetic sebum (containing materials corresponding to those found in natural sebum) was then sprayed on each switch until a predetermined weight of sebum was applied. The switches were then allowed to equilibrate at approximately 27° C. and 80% relative humidity.

The switches were paired as detailed in Table II, below. Each pair of switches was then evaluated by ten expert judges, and rated on a scale ranging from "not soiled" to "heavily soiled". Higher scores indicated less soiled (cleaner) switches. The pairings and results are set forth below.

TABLE II

| Pair | Compositions tested | Degree of Cleanliness |
|---|---|---|
| 1 | A - vehicle only | 50 |
|   | B - vehicle + dimethicone copolyol | 57 |
| 2 | A - vehicle only | 57 |
|   | C - vehicle + silicone conditioner | 55 |
| 3 | A - vehicle only | 66 |
|   | D - present invention | 75 |
| 4 | C - vehicle + silicone conditioner | 49 |
|   | D - present invention | 63 |

The scores for Pairs 1, 3 and 4 reflect significant differences in cleanliness/soiling (between switches in each pair) at a confidence level. This data thus demonstrates that the compositions of the present invention (such as Composition D) exhibit lower soiling of hair after use than similar compositions that do not contain dimethicone copolyol.

What is claimed is:

1. A conditioning composition, useful on human hair, comprising:
   (a) from about 0.1% to about 10% of non-volatile polydimethyl siloxane having the following formula $$(CH_3)_3SiO + Si(CH_3)_2O \xrightarrow{}_n Si(CH_3)_3$$

wherein n is from 20 to 7,000;
   (b) a vehicle for the non-volatile polydimethyl siloxane which consists of:
      (A) from about 0.1% to about 10% of a lipid material; and
      (B) from about 0.05% to about 5% of a cationic surfactant material;
   (c) from about 0.1% to about 2.0% of a substantially non-depositing anti-resoiling agent consisting of a dimethicone copolyol; and
   (d) the balance of water.

2. A conditioning composition, according to claim 1, wherein said lipid vehicle material is selected from the group consisting of fatty alcohols, fatty esters, and mixtures thereof.

3. A conditioning composition according to claim 2, wherein said lipid vehicle material contains carbon chains of from 12 to 18 carbon atoms in length.

4. A conditioning composition, according to claim 3, comprising from about 1% to about 3% of said lipid vehicle material.

5. A conditioning composition, according to claim 1, wherein said cationic surfactant vehicle material contains carbon chains of from 12 to 18 carbon atoms in length.

6. A conditioning composition, according to claim 5, comprising from about 0.2% to about 3% of said cationic surfactant vehicle material.

7. A conditioning composition, according to claim 1, comprising from about 0.25% to about 1.5% of said silicone conditioning agent.

8. A conditioning composition, according to claim 4, wherein said lipid vehicle material is selected from the group consisting of cetyl alcohol, stearyl alcohol, cetyl palmitate, glycerol monostearate, and mixtures thereof.

9. A conditioning composition, according to claim 6, wherein said surfactant vehicle material is a quaternary ammonium salt.

10. A conditioning composition, according to claim 6, wherein said cationic surfactant vehicle material is a fatty amine.

11. A conditioning composition, according to claim 9, wherein said cationic surfactant vehicle material is di(hydrogenated tallow) dimethyl ammonium chloride.

12. A conditioning composition, according to claim 1, additionally comprising an optional surfactant material selected from the group consisting of anionic, nonionic and amphoteric surfactants.

13. A conditioning composition, according to claim 12, wherein said optional surfactant material is a nonionic surfactant.

14. A conditioning composition, according to claim 1, wherein said composition is buffered to a pH in the range of from about 3 to about 10.

15. A conditioning composition, according to claim 2, additionally comprising a nonionic polymeric thickener.

16. A method of conditioning hair comprising the steps of:
(a) applying from about 1 gram to about 60 grams of a composition according to claim 1, to freshly shampooed hair; and
(b) rinsing said composition from said hair.

* * * * *